(12) United States Patent
Karazivan

(10) Patent No.: US 8,814,571 B2
(45) Date of Patent: *Aug. 26, 2014

(54) INTERPROXIMAL TOOTH COATING APPLICATOR

(75) Inventor: Naim Karazivan, Repentigny (CA)

(73) Assignee: Dentsply Canada Ltd., Woodbridge, ON (CA)

(*) Notice: Subject to any disclaimer, the term of this patent is extended or adjusted under 35 U.S.C. 154(b) by 0 days.

This patent is subject to a terminal disclaimer.

(21) Appl. No.: 12/425,658

(22) Filed: Apr. 17, 2009

(65) Prior Publication Data

US 2010/0203467 A1 Aug. 12, 2010

Related U.S. Application Data

(63) Continuation of application No. 09/983,829, filed on Oct. 26, 2001, now Pat. No. 7,537,450, which is a continuation-in-part of application No. 09/301,767, filed on Apr. 29, 1999, now abandoned.

(51) Int. Cl.
*A61C 15/00* (2006.01)

(52) U.S. Cl.
USPC .............................................. 433/215; 433/80

(58) Field of Classification Search
USPC .................. 433/80, 215, 226; 132/321, 329
See application file for complete search history.

(56) References Cited

U.S. PATENT DOCUMENTS

| 185,666 A | 12/1876 | Brown |
| 1,637,153 A | 7/1927 | Lawton |
| 2,611,182 A | 9/1952 | Tofflemire |
| 2,646,622 A | 7/1953 | Christie et al. |
| 2,667,443 A | 1/1954 | Ashton |
| 2,700,220 A | 1/1955 | Peterson |

(Continued)

FOREIGN PATENT DOCUMENTS

| DE | 4317370 | 12/1994 |
| EP | 0085027 | 8/1983 |

(Continued)

OTHER PUBLICATIONS

Plastic Sealing of Proximal Surfaces of Teeth, A New Technic, J.M. Davila, R.F. Sisca, N. Tinanoff, D.V. Provenza, Journal of the Baltimore College of Dental Surgery 30(1) 1975, pp. 40-47.

(Continued)

*Primary Examiner* — Ralph Lewis
(74) *Attorney, Agent, or Firm* — Anglehart et al.

(57) ABSTRACT

The present invention relates to a tooth coating applicator (10), typically in the form of a strip (11), and a method for applying a dental sealant to a surface of a tooth (T), and specifically to the interproximal surface (S) thereof. The applicator (10) is elongated and is adapted to be typically inserted into an interproximal space (I) defined between a pair of adjacent teeth (T, T') and to be gradually slid against a dental surface of one of the teeth. The applicator (10) comprises a series of substrates (12, 14, 16, 18, 20, 22, 24, 26, 28, 30, 36, 40, 42) for generally successively removing debris and deposits from the interproximal dental surface (S), etching (20) the dental surface (S), washing (22) the dental surface (S), drying (24, 26) the dental surface (S), carrying (28) the sealing agent and applying the sealing agent to the dental surface (S), exerting pressure (30) on the dental surface (S) during the hardening of the sealing agent, and polishing (36, 38) the dental surface (S) and its cured sealing agent.

3 Claims, 1 Drawing Sheet

(56) References Cited

U.S. PATENT DOCUMENTS

| | | | |
|---|---|---|---|
| 3,421,222 A * | 1/1969 | Newman | 433/36 |
| 3,482,314 A | 12/1969 | Tofflemire | |
| 3,699,979 A | 10/1972 | Muhler et al. | |
| 3,754,332 A | 8/1973 | Warren, Jr. | |
| 3,838,702 A | 10/1974 | Standish et al. | |
| 3,897,795 A | 8/1975 | Engel | |
| 3,897,796 A | 8/1975 | Erickson | |
| 3,942,539 A | 3/1976 | Corliss et al. | |
| 3,986,261 A | 10/1976 | Faunce | |
| 4,450,849 A | 5/1984 | Cerceo et al. | |
| 4,563,152 A | 1/1986 | McClure | |
| 4,570,653 A | 2/1986 | Wolf | |
| 4,778,385 A | 10/1988 | Herrin | |
| 4,795,527 A | 1/1989 | Cohen | |
| 4,913,176 A | 4/1990 | DeNiro | |
| 4,941,487 A | 7/1990 | VanBeneden | |
| 5,035,615 A | 7/1991 | Din | |
| 5,246,371 A | 9/1993 | Fischer | |
| 5,316,028 A | 5/1994 | Flemming | |
| 5,330,353 A | 7/1994 | Wavrin | |
| 5,365,874 A | 11/1994 | Dorfman | |
| 5,527,181 A | 6/1996 | Rawls | |
| 5,560,377 A | 10/1996 | Donovan | |
| 5,582,195 A | 12/1996 | Nagel | |
| 5,647,746 A | 7/1997 | Chipman | |
| 5,730,592 A | 3/1998 | Meyer | |
| 5,788,487 A | 8/1998 | Meyer | |
| 5,908,296 A | 6/1999 | Kipke et al. | |
| 5,989,032 A * | 11/1999 | Reynaud et al. | 433/224 |
| 5,997,302 A | 12/1999 | Alpert | |
| 6,007,334 A | 12/1999 | Suhonen | |
| 6,146,687 A | 11/2000 | Desai | |
| 6,482,005 B1 | 11/2002 | Summer et al. | |

FOREIGN PATENT DOCUMENTS

| | | |
|---|---|---|
| EP | 0087022 | 8/1983 |
| EP | 0491654 | 6/1992 |
| WO | 9740774 | 11/1997 |

OTHER PUBLICATIONS

Patent Abstracts of Japan, vol. 013, No. 134 (C-581), Apr. 4, 1989 & JP 63 300756 A (Ryoji Ikejiri), Dec. 7, 1998 abstract.

Examination report of European patent application No. 00922372.8 with related pending claims 1-45, May 12, 2006.

Examiner's report on Australian patent application No. 2008207459 dated on Dec. 22, 2011 with related pending claims 1-14.

Examiner's report on Australian patent application No. 2008207459 dated on Aug. 9, 2010 with related pending claims 1-85.

File Wrapper of U.S. Appl. No. 10/296,246-P1009US00, filed Dec. 9, 2002.

International preliminary report of PCT/CA01/00824-P1009, (Feb. 21, 2002).

International search report of PCT/CA01/00824-P1009 with claims, (Dec. 13, 2001).

Office Action for Canadian patent application No. 2,372,293 (Apr. 18, 2008) with related pending claims, 1-85.

Office Action for Canadian patent application No. 2,372,293 (Jul. 7, 2010) with related pending claims 1-55.

Office Action for Canadian patent application No. 2,372,293 (Sep. 14, 2009) with related pending claims 1-62.

Office Action for Canadian patent application No. 2,411,917 (20080717) P1009CA01 with related pending claims 1-88.

Office Action for Canadian patent application No. 2,411,917 (20090914) P1009CA01 with related pending claims 1-59.

Office Action for Chinese patent application No. 00809469.1 (Feb. 23, 2009) with related claims in English.

Office Action for Japanese patent application No. 2000-614912 (Oct. 14, 2008) with related pending claims 1-43 in english.

Response to Examination report of European patent application No. 00922372.8 (Mar. 27, 2007).

Response to Examiner's report on Australian patent application No. 2008207459 dated on Oct. 10, 2011.

Response to Examiner's report on Australian patent application No. 2008207459 dated on Apr. 16, 2012.

Response to Examiner's report on Australian patent application No. 2008207459 dated on Oct. 17, 2011.

Response to Office Action for Canadian patent application No. 2,372,293 (Jan. 20, 2009).

Response to Office Action for Canadian patent application No. 2,372,293 (Mar. 15, 2010).

Response to Office Action for Canadian patent application No. 2,372,293 (Jan. 7, 2011).

Response to Office Action for Canadian patent application No. 2,411,917 (Jan. 19, 2009) P1009CA01.

Response to Office Action for Canadian patent application No. 2,411,917 (Mar. 15, 2010) P1009CA01.

* cited by examiner

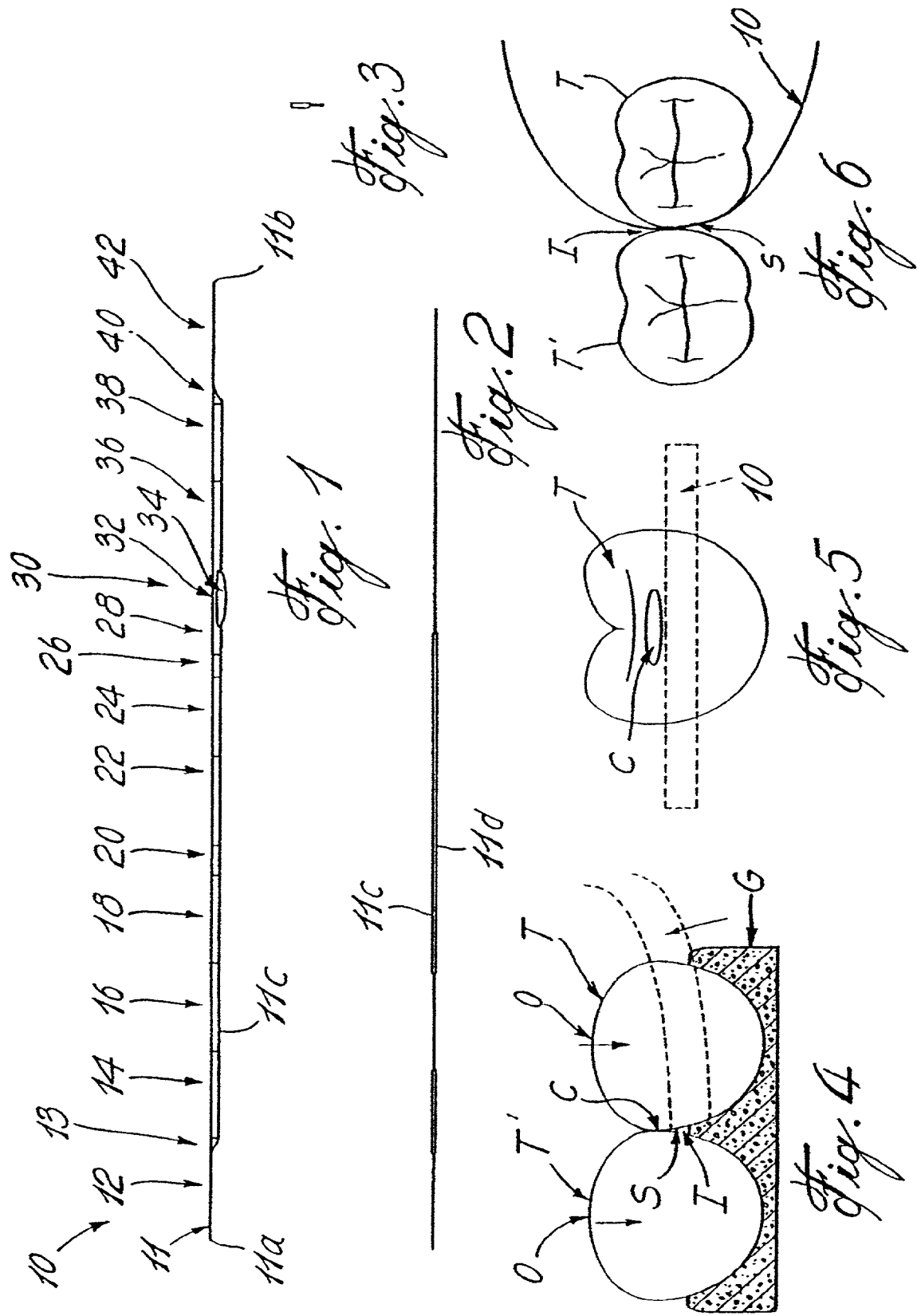

US 8,814,571 B2

INTERPROXIMAL TOOTH COATING APPLICATOR

BACKGROUND OF THE INVENTION (a) Field of the Invention

The present invention relates to an applicator for applying a dental sealant. The present invention relates particularly to an applicator for applying a dental sealant to an interproximal surface of a tooth.

(b) Description of Prior Art

Dental sealants consist of plastic films that are applied to the chewing surfaces of teeth to seal the fissures therein and prevent caries.

The surface of the teeth is generally made of enamel, which is negatively charged and is normally covered with a biofilm consisting of physiological fluid and bacteria.

In order to insure bonding of the sealant material with the enamel, the dental surface to be treated is first isolated to prevent saliva contamination, cleaned with a water-washable cleansing agent and removed of plaque. The dental surface is dried and an etchant is applied onto the surface for a period of time to create pores in the enamel. The etched surface is then washed with water, dried and kept from contamination with saliva. The sealant material is then applied, for instance with a brush or a dropper, onto the dental surface according to the manufacturers' instructions. Thereafter the sealant is cured, thereby mechanically bonding with the enamel surface. Finally, the sealant may be polished to obtain a smooth finish.

A problem with dental sealants is that they cannot be applied on interproximal dental surfaces, due to a difficult access thereto and to a risk of contaminating the sealant material with the saliva, or other fluids, accumulated in the interproximal space between adjoining teeth.

It is known to use dental floss or tape to remove food debris, plaque and the like from interproximal dental surfaces. Dental floss is prepared from nylon or other suitable threads woven together to form a larger thread that may be coated with an insoluble wax such as paraffin.

It is also known to impregnate dental floss with chemicals such as cleaning agents. For example, reference is made to U.S. Pat. No. 185,666 issued to Brown, U.S. Pat. No. 2,667,443 to Ashton, U.S. Pat. No. 3,699,979 to Muhler et al., U.S. Pat. No. 3,942,539 to Corliss et al., U.S. Pat. No. 4,819,675 to Wilkinson, U.S. Pat. No. 4,941,487 to VanBeneden, U.S. Pat. No. 5,165,913 to Hill et al. and U.S. Pat. No. 5,665,333 to Homola et al.

It must be noted that there are presently no durable preservative treatments against starting interproximal caries; in such cases, dentists either do not treat the caries while subsequently monitoring the same, treat the caries with costly and invasive restorative techniques or treat with a non-durable and expensive treatment the caries using an anti-microbial product.

It would therefore be highly desirable to provide a device with which one could apply a sealing agent to an interproximal dental surface.

It would also be highly desirable to provide a method for applying a sealing agent to an interproximal dental surface.

SUMMARY OF THE INVENTION

It is therefore an aim of the present invention to provide a device with which one can apply a sealing agent to a surface of a tooth, for instance to an interproximal surface thereof.

It is also an aim of the present invention to provide a tooth coating applicator in the form of an elongated strip which is displaced along the tooth surface to be treated.

It is a further aim of the present invention to provide such a tooth coating applicator which comprises a series of substrates, for instance, for generally successively removing debris and deposits from the dental surface, etching the dental surface, washing the dental surface, drying the dental surface, applying the sealing agent to the dental surface, exerting pressure on the dental surface during the hardening of the sealing agent, and polishing the dental surface and its cured sealing agent. The sealant may also be applied in an already hardened state.

It is a still further aim of the present invention to provide a method for applying a sealing agent to a dental surface, e.g. an interproximal dental surface.

It is a still further aim of the present invention to provide a device and a method for applying a sealing agent to a dental surface having an early stage caries to stop, or at least delay, a further development thereof.

It is also an aim of the present invention to provide a dispensing apparatus for storing and dispensing such a device.

Therefore, in accordance with the present invention there is provided a method for applying a sealing agent to a dental surface of a tooth, said method comprising:

providing an elongated strip comprising a substrate which is pre-formed substantially along a shape of the dental surface to be treated, said substrate being adapted to apply a sealing agent to the dental surface;

placing said substrate and said sealing agent in contact with the dental surface; and handling said substrate such that at least a part of said sealing agent is transferred onto the dental surface.

Also in accordance with the present invention, there is provided a method for applying a sealing agent to a dental surface, said method comprising:

providing an elongated member provided with at least two sections;

preparing the dental surface using one of said sections; and applying said sealing agent to the dental surface using the other one of said sections.

Still in accordance with the present invention, there is provided a method for applying a sealing agent to a dental surface of a tooth, said method comprising:

providing an elongated strip comprising a substrate which is adapted to substantially conform to a shape of the dental surface to be treated, said substrate being also adapted to apply a sealing agent to the dental surface;

placing said substrate and said sealing agent in contact with the dental surface; and handling said substrate such that at least a part of said sealing agent is transferred onto the dental surface.

Still further in accordance with the present invention, there is provided a device for applying a sealing agent to a dental surface, said device being adapted to be positioned against, or adjacent to, the dental surface, said device comprising a first substrate adapted to substantially conform to a shape of the dental surface to be treated and being also adapted to apply a sealing agent to the dental surface, for transferring at least a part of the sealing agent onto the dental surface when said first substrate is in position against the dental surface.

Still further in accordance with the present invention, there is provided a device for applying a sealing agent to a dental surface, said device being adapted to be positioned against, or adjacent to, the dental surface, said device being elongated and comprising successive first and second substrates, said first substrate being adapted to apply a sealing agent to the dental surface, for transferring at least a part of the sealing agent onto the dental surface when said first substrate is in position against the dental surface, and said second substrate being adapted to prepare the dental surface.

Still further in accordance with the present invention, there is provided a method for applying a sealing agent to a dental surface of a tooth, said method comprising:

providing a substrate adapted to apply a sealing agent to the dental surface to be treated;

placing said substrate and said sealing agent in contact with the dental surface;

handling said substrate such that at least a part of said sealing agent is transferred onto the dental surface; and shaping the sealing agent on the dental surface.

Still further in accordance with the present invention, there is provided a system for applying a sealing agent to a dental surface, comprising a first device adapted to be positioned against, or adjacent to, the dental surface, said first device being adapted to apply a sealing agent to the dental surface, for transferring at least a part of the sealing agent onto the dental surface, and a second device for shaping the sealing agent on the dental surface.

Still further in accordance with the present invention, there is provided a method for applying a sealing agent to a dental surface of a tooth, said method comprising:

providing a substrate adapted to apply a sealing agent to the dental surface;

placing said substrate in contact with, or adjacent to, the dental surface; and supplying said sealing agent between said substrate and the dental surface such that at least a part of said sealing agent is applied onto the dental surface.

For the purpose of the present invention the following terms are defined below.

The expression "interproximal surface" is intended to mean a tooth surface extending adjacent another tooth, such as a surface around a contact area of two adjoining teeth, but also means the interproximal surface of a tooth which does not have an immediately adjacent tooth next to it (such as when there is a significant space laterally of the tooth due, for instance, to a missing tooth). The method and device of the present invention are also adapted for use on other surfaces of the tooth, e.g. the labial, the buccal and the lingual surfaces.

The expression "absorbent material" is intended to mean a material suitable for absorbing a fluid, such material including linen, silk, cotton, nylon and other synthetic or natural fibres. The material may be prepared in yarns which may be braided, spun, thrown or fused.

The term "fluid" includes liquids which may be naturally present or inserted in the mouth such as water, oil, chemical agents and physiological fluids such as blood, saliva and crevicular liquids, and which may interfere with the agents used during the sealing process.

The term "matter" includes substances which may be present on a dental surface such as food debris, plaque, bacteria, saliva and the like.

The expression "sealing agent" includes, amongst others, ultraviolet light-cured, chemically or self-cured and visible light-cured acid-etched sealant material, and other suitable enduring, inert, hydrophobic, protective agents which may be sealed onto a dental surface and which may remain on the dental surface over an extended period of time. The sealing agent may be in a liquid or gel form and may include sealing agents containing fluoride. Also, the sealing agent may take the form of a film, such as a resin film, a gold sheet, or other made of any other suitable material.

The expression "etching agent" includes, amongst others, acid solutions such as phosphoric, citric and maleic acids, which may be applied on the enamel of a tooth for a period of time for preparing same to bond with a sealing agent. The etching agent may be removed such as by washing it with a washing agent such as water or by neutralising it with an acid-neutralising agent compatible with the subsequent application of the sealing agent. The washing agent may be applied on a section of the substrate such as with a syringe, or may be injected directly on the dental surface, for instance, with a syringe.

The expression "hydrophilic agent" includes substances such as primers which may be used to absorb moisture which may be present on the dental surface and so increase the bonding strength of the sealant to the dental surface.

The expression "activator agent" includes substances, such as activators for dental resins (e.g. activator of Scotchbond™ Multi-Purpose Plus 3M), that may be used to accelerate the curing process of the resin.

The term "cavity" is intended to mean an area of decay in a tooth resulting from caries.

The tooth coating applicator of the present invention may allow to reach the interproximal dental surface, keep the same isolated from fluids, prepare the same for the application of the sealing agent and apply the sealing agent thereto.

Accordingly, the present invention provides a device for preparing an interproximal dental surface and for then applying a sealing agent thereto.

The device may be of any material, such as a flexible material, suitable for insertion into the interproximal space and to be slid or held against a dental surface.

The dimension of the device is sufficiently narrow to permit insertion thereof into the interproximal space. In general, the space between teeth ranges from about 0 mm to about 1 mm. In general, the interproximal space is filled with the patient's gum which is tightly apposed against the teeth surface. Because of the elasticity of the gum tissue, a floss or strip may be inserted between the gum and the tooth. The width of the substrate may vary from about 0.5 mm to about 10.0 mm. The thickness of the substrate may vary from about 0.01 mm to about 1.5 mm. A preferred thickness is about 0.05 mm.

The device may comprise a first section for preparing the interproximal dental surface and a second section adapted to carry a sealing agent to the dental surface. The first section may prepare the dental surface by drying.

The device may comprise a tooth coating applicator, such as a strip, including the just mentioned second section, and possibly also the just mentioned first section. Each step required for applying the sealing agent in an acceptable fashion on the dental surface may correspond to a section or substrate of the tooth coating applicator or several steps can be done on the same section.

Accordingly, the tooth coating applicator of the present invention may comprise a plurality of substrates. For instance, the substrates may be conveniently provided on a single strip. Each substrate may have a distinct function in the overall application of the sealing agent to the dental surface.

The substrates may be adjacent one another. Alternatively, the substrates may be spaced apart from each other.

Alternatively, some substrates may be provided on one side of the applicator while some other substrates may be provided on the opposite side, or on both sides, of the applicator.

Some of the substrates may be coloured to help the user distinguish between the different substrates and their respective functions.

BRIEF DESCRIPTION OF THE DRAWINGS

Having thus generally described the nature of the present invention, reference will now be made to the accompanying drawings, showing by way of illustration, a preferred embodiment thereof, in which like numerals refer to like elements, and in which:

FIG. 1 illustrates in a front elevational view a tooth coating applicator in accordance with a first embodiment of the present invention;

FIG. 2 illustrates in a top plan view the tooth coating applicator shown in FIG. 1;

FIG. 3 illustrates in an end elevational view the tooth coating applicator shown in FIG. 1;

FIG. 4 illustrates in an enlarged front elevational view a pair of adjoining teeth with the tooth coating applicator of FIG. 1 disposed therebetween;

FIG. 5 illustrates in an enlarged side elevational view a tooth and the tooth coating applicator of FIG. 1 extending under a contact area of adjoining teeth; and FIG. 6 illustrates in an enlarged top plan view the tooth coating applicator and the pair of adjoining teeth of FIG. 4.

DETAILED DESCRIPTION OF THE PREFERRED EMBODIMENTS

Referring to FIGS. 1 to 4, there is illustrated a first embodiment of a tooth coating applicator in accordance with the present invention, which consists of fifteen (15) substrates. The tooth coating applicator is identified with reference numeral 10 and is used for applying a coating, such as a dental sealant, to an interproximal surface S of a tooth such as by inserting the coating applicator 10 between a pair of adjacent teeth T and T', that is through an interproximal space I defined therebetween.

The tooth coating applicator 10 comprises an elongated strip 11 which allows access to the interproximal space I and to the interproximal dental surface S and isolates the interproximal area during the process, as will be described in details hereinafter. This permits for the sealing agent to retain its integrity and to be adequately applied to the dental surface S. The strip 11 has a first end 11a and an opposed second end 11b, a front side 11c and an opposed rear side 11d. The front and rear sides 11c and 11d are joined by thin elongated edges. The strip 11 has a width of approximately 2 mm and is made of a woven fibrous material.

The strip 11 is provided with a first substrate 12 disposed adjacent the first end 11a. The first substrate 12 allows the user to insert the tooth coating applicator 10 in and through the interproximal space I, through and under a contact area C between the adjoining teeth T and T' and against the interproximal dental surface S to be treated. The first substrate 12 may be used to clean the surface S and to verify its condition. The first substrate 12 which is used to pull the strip 11 into the interproximal space I and against the dental surface S is typically constituted of dental floss (or other thread-like material) having, for instance, a length of between 5 and 15 cm. The yarn may be made of any suitable natural or synthetic fibre such as cotton, silk, linen, nylon, polyester or acrylic or mixtures thereof.

The first substrate 12 may be slid between the adjoining teeth T and T' towards the patient's gum, and through and past the contact area C, and finally into the interproximal space I.

It is also contemplated to have the first substrate 12 in the form of a strip. The strip would then itself be forced through and past the contact area C.

The first substrate 12 may also be positioned in the interproximal space I by inserting the end 11a thereof in a direction parallel to the occlusal surface O of the teeth; in other words, the end 11a would be threaded through the interproximal space I thereby avoiding the need to pass the tooth coating applicator 10 through the contact area C. In such a case, the end 11a may be made substantially rigid to facilitate its introduction in and through the interproximal space I.

The first substrate 12 may be also made of a thread, yarn, wire or band of any suitable material such as dental floss, silk, nylon, metal or the like.

Adjacent the first substrate 12, a second substrate 13 connects the first substrate 12 to a third substrate 14. The second substrate 13 which has a flaring shape allows gradual positioning of the strip 11 and facilitates insertion thereof under the area of contact C of the adjoining teeth T and T'.

The third substrate 14 is mainly used to absorb the fluids present on the dental surface S. The third substrate 14 which is constituted of cotton (or other absorbent material) and which has a length of approximately 6 cm is used primarily as a first cleaning medium for the dental surface S, by abrasion or absorption of the plaque and liquids present on this surface S.

A fourth substrate 16 is disposed adjacent the third substrate 14. The fourth substrate 16 acts as an abrasive used to mechanically break the mineral deposits and plaque present on the dental surface S. The fourth substrate 16 is made of an abrasive material such as conventional abrasive materials used to polish dental fillings. The fourth substrate 16 has a length of approximately 4 cm.

A fifth substrate 18 is disposed adjacent the fourth substrate 16. The fifth substrate 18 absorbs the plaque residues resulting from the breaking of the plaque and the fluids (e.g. blood, saliva, crevicular liquids) present on the dental surface S. The fifth substrate 18 is made of 6 cm of cotton, or any other suitable absorbent material.

A sixth substrate 20 is disposed adjacent the fifth substrate 18. The sixth substrate 20 is adapted to absorb and then carry an etching agent (e.g. different types of acids in the form of liquids or gels) to the dental surface S. The sixth substrate 20 is made of cotton (or any other suitable absorbent material) and has a length of approximately 1 cm. This substrate may also be pre-impregnated with the etching agent. In the present invention, the term "pre-impregnated" is used generally in the sense that a product has been impregnated in a given substrate at the manufacturing level of the tooth coating applicator 10. Some of the pre-impregnated products, such as the sealing agent, may be in the form of two separate substrates separated on the strip 11 and which can be mixed, for instance by rubbing them successively on the tooth surface S, when the user is ready to apply the product, e.g. the sealing agent, thereon. On the other hand, it is rather contemplated that the user impregnates the substrates just prior to using the tooth coating applicator 10, that is before the tooth coating applicator 10 is introduced in the interproximal space or more generally put into contact with the dental surface to be treated.

A seventh substrate 22 is disposed adjacent the sixth substrate 20. The seventh substrate 22 is adapted to absorb and then carry water applied thereon to the dental surface S (for instance with a syringe), for removing the etching agent therefrom and absorbing it. The seventh substrate 22 is made of cotton, or any other suitable absorbent material, and has a length of approximately 6 cm.

An eighth substrate 24 is disposed adjacent the seventh substrate 22. The eighth substrate 24 absorbs the residual water and etching agent. The eighth substrate 24 is made of cotton, or any other suitable absorbent material, which may contain an absorbent substance (e.g. powder) and which has a length of approximately 6 cm.

A ninth substrate 26 is disposed adjacent the eighth substrate 24. The ninth substrate 26 is adapted to absorbs a hydrophilic agent ("primer") and/or an activator agent to be applied thereon by the user and then deposited onto the dental surface S for absorbing the residual moisture on the dental surface S. The hydrophilic agent and/or the activator agent may also have been pre-impregnated on this ninth substrate 26. The hydrophilic agent or primer may be any of those made by the Kerr Company or by 3M. The ninth substrate 26 is made of cotton, or any other suitable absorbent material, and has a length of approximately 2 cm.

A tenth substrate 28 is disposed adjacent the ninth substrate 26. The tenth substrate 28 is adapted to absorb the sealing agent applied thereon by the operator and to then carry the sealing agent to the dental surface S. This tenth substrate 28 may also be pre-impregnated with the sealing agent (possibly in two different substances, as mentioned hereinabove). The sealing agent may be A+B of the Kerr Company or 3M or sealant Delton A+B of the Dentsply Company. The tenth substrate 28 is made of cotton, or any other suitable absorbent material and has a length of approximately 2 cm.

An eleventh substrate 30 is disposed adjacent the tenth substrate 28 and includes adjacent first and second sections 32 and 34, respectively. The eleventh substrate 30 is made of a smooth material, such as a stainless steel strip (e.g. tofflemire strip) or a celluloid strip, having or not a slightly domed (convexly rounded) shape, elastic or not. The eleventh substrate 30 is used to apply pressure on the sealing agent to render it thin before its polymerisation and to give it a smooth mould during polymerisation. The first section 32 facilitates the sliding of the eleventh substrate 30 when passing under the area of contact C between the adjoining teeth T and T'. The first section 32 is made of plastic. The second section 34 facilitates the sliding of the eleventh substrate 30 against the dental surface S to be treated. The second section 34 is also made of plastic. Alternatively, the second section 34 may be made of an elastic and smooth material such as a plastic wrap (e.g. Saran-Wrap™ like material).

It is possible for the eleventh substrate 30 to replace the tenth substrate 28 in carrying the sealing agent and/or the activator agent (it is noted that the activator agent may be applied using the ninth, tenth or eleventh substrates 26, 28 and 30, respectively) to the dental surface S. This substrate 30 may or may not have orifices on its side designed for the injection of products and/or for the evacuation of products. The eleventh substrate 30 has a length of approximately 2 cm.

Alternatively, the sealing agent may take the form of a releasable film applied onto the eleventh substrate 30 for application on the dental surface S. Such a film provides a sealing agent having an homogenous finish. The film may be made of any suitable material such as an adhesive resin, a sealing agent, a composite, a glass ionomer, a gold film, or any other biocompatible resin or material. The film which is mounted on the smooth section will detach from the eleventh substrate 30 and adhere to the surface S of the tooth T thereby allowing for a perfectly smooth and homogeneous external finish and ensuring for a complete coverage of the tooth surface S even if the adhesion is not very strong, for instance in cases of the beginning of a caries thereat. The tooth coating applicator 10 can then thus be used for the treatment of caries (in addition to be used in the prevention thereof).

The eleventh substrate 30 may contain optic fibres which allow for the use of a light polymerising sealant.

A twelfth substrate 36 is disposed adjacent the eleventh substrate 30. The twelfth substrate 36 removes the excess of sealing agent and polishes porous or uneven portion of the applied sealing agent. The eleventh substrate is made of a medium grade abrasive and has a 4 cm length. An independent sanding strip may be used.

A thirteenth substrate 38 is disposed adjacent the twelfth substrate 30. The thirteen substrate 38 is used for the final polishing of the applied sealing agent and can have its abrasive distributed only along the longitudinal borders thereof such that polishing is effected only at the upper and lower edges of the sealant; in such a case, there is no polishing of the central area of the sealant by the substrate 38. The thirteen substrate 38 is made of a fine grade abrasive and has a length of about 4 cm. An independent sanding strip may be used.

A fourteenth substrate 40 joins the thirteenth substrate 38 to a fifteenth substrate 42. The fourteenth substrate 40 which has a tapering configuration allows gradual removing of the strip 11 from the interproximal space I.

The fifteenth substrate 42 is disposed adjacent the fourteenth substrate 40 and up to the second end 11b. The fifteenth substrate 42 is used for verifying the applied sealing agent and removing the residual debris of sealing agent, which may still be present. The fifteenth section 42 is made of dental floss (e.g. 5 to 15 cm).

The strip 11 thus permits for the interproximal dental surface S to be reached, for this surface S to be maintained sufficiently isolated, for the surface S to be treated and for the sealing agent to be applied thereto.

The sealant application substrate 28 and more importantly the eleventh substrate 30 may be anatomically shaped, that is pre-formed along the curved shape of the tooth surface S to be treated or capable of following this curved shape, so as to conform or adapt to this tooth surface's shape and thus ensure proper coverage of sealant on the complete tooth surface S. Alternatively, the substrates 28 and especially 30 may be made of a material capable of substantially conforming to the shape of the tooth surface S, such as by having a material which is flexible, and perhaps elastic, thereby avoiding excess sealant at the margins of the sealed area and thus providing a smooth transition between the sealed area and the adjacent tooth surface, and hence avoid plaque accumulation thereat. The shaping of the sealant may possibly be carried out by an appropriate tool, instead of by substrate 30.

Additionally, the sealant application area 28 may include a cushion on its gingival side to allow the substrate 28 to conform to the tooth surface S in the event that the tooth surface S, adjacent the gum G, defines depressions. It is noted that other substrates may be pre-formed in the shape of the contour of the tooth surface S, as for the sealing application substrate 28 mentioned hereinabove, although this is of lesser importance in the case of these other substrates.

The sealant application substrate 28 may also define a depression to provide a space for the sealant on the tooth surface S. In this case, an orifice may be defined through the substrate 28 so that products such as the sealant can be injected into this space.

The sealant application substrate 28 of the strip 11 may include an occlusal extension passing through the contact area C between the two teeth T and T'. A guide line or mark may be provided on the sealant application substrate 28 to facilitate the positioning of the strip 11 with respect to the contact area C.

It is possible to use a sealant (e.g. a glass ionomer) which does not require preparatory steps, thereby eliminating the etching and rinsing steps and rendering the drying step less important in view of the characteristics of the glass ionomer.

It is also possible that the sealant application substrate 28 of the strip 11 includes portions containing a polymerisation inhibiting product (e.g. urethane absorbent+H2O, perforations, 3M™ absorbent), or an absorbent product allowing for the absorption of excess adhesive material. The aim of this is to allow a hardening of the sealant only in the desired area, thereby limiting the need to remove post-treatment excesses.

An additional substrate may be provided, after the final polishing substrate 38 for applying anti-microbial and/or anti-caries substances, e.g. fluoride, thereto such as to reinforce the tooth's enamel that has been etched.

Some of the substrates may be coloured to help the user distinguish between the different substrates and their respective functions. Some of the substrates may be pre-impregnated with their respective product(s) thereby enabling the operator to save time and to simplify the task.

Referring now to FIGS. 4 and 5, the tooth coating applicator 10 operates as follows. For each step, the user grips the tooth coating applicator 10 on each side of the substrate being operatively used between the two adjoining or adjacent teeth T and T' to carry out a given operation to the dental surface S. The tooth coating applicator 10 is generally continuously in position between the teeth T and T' and is gradually slid through the interproximal space I (in a direction generally parallel to the occlusal surface O) such as to allow each substrate to perform, in order, its respective function. Initially, the tooth coating applicator 10 is positioned between the two adjoining teeth T and T' by sliding it in the direction of a patient's gum G, through the contact area C between the adjoining teeth T and T'.

Once in position against the dental surface S to be treated, the user slides the first substrate 12 against the dental surface S in a generally parallel direction relative to the occlusal plane, to approach the second substrate 13 to the dental surface S. A teeth separator (not shown), e.g. a stainless steel disc, may be used while the treatment is dispensed. The user slides the second substrate 13 against the dental surface S, followed by the third substrate 14, for cleaning the dental surface S.

The user slides the fourth substrate 16, for breaking the mineral deposits which may be present on the dental surface S. The user slides the fifth substrate 18 against the dental surface S and maintains same against it to carry out the drying thereof.

The user deposits an etching agent (if this etching agent has not been pre-impregnated) onto the sixth substrate 20 and slides the same against the dental surface S. After the etching agent has been left to react with the dental surface S, the user injects water on the seventh substrate 22. The user then slides the seventh substrate 22 to wash the etching agent from the dental surface S.

While the seventh substrate 22 is maintained against the dental surface S, the user applies a hydrophilic agent and/or activator agent onto the ninth substrate 26.

While the user maintains the seventh substrate 22 against the dental surface S, a sealing agent is applied onto the tenth substrate 28 (or on second section 34 of the eleventh substrate 30 in the event that the latter is used, instead of the tenth substrate 28, to carry the sealing agent to the dental surface S).

Thereafter, the user uses an air syringe to inject pressurised air between the eighth substrate 24 and the dental surface S to dry the area, and then slides the eighth substrate 24 against the dental surface S to dry the same of residual water. The user then slides the ninth substrate 26 against the dental surface S for removing residual moisture therefrom.

The tenth substrate 28 is then slid against the dental surface S for application of the sealing agent thereto.

While the sealing agent is still in its uncured phase (i.e. liquid or gel), the user slides the eleventh substrate 30 against the dental surface S under the contact area C, to prevent the obstruction thereof by the sealing agent. The user maintains the eleventh substrate 30 against the dental surface S until the sealing agent has sufficiently polymerised (or hardened).

Alternatively, the user may, while maintaining the eleventh substrate 30 against the dental surface S, inject directly between the eleventh substrate 30 and the dental surface S, the sealing agent using a syringe. Therefore, in such a case, the clinician, instead of first applying the sealant on the applicator 30 and then sliding it against the tooth surface S, puts the applicator 30 against the surface S and then applies the sealant directly between the eleventh substrate 30 and the dental surface S, such as by letting a drop of sealant seep in, and then distribute along, the interface strip-tooth surface. In fact, as for the just described sealant, the various products may, instead of being applied directly onto a given substrate, be injected directly between such a given substrate, which is in position against the dental surface being treated, and this dental surface. A back-and-forth sliding movement may be imparted to the substrate, after the product has been applied between the substrate and the tooth T, to ensure a better distribution of the product on the tooth surface S.

The user then polishes the applied sealant material by sliding the twelfth and thirteenth substrates 36 and 38 against it. The fifteenth substrate 42 is used to verify the dental surface S, that is to verify that the sealing agent has been appropriately applied. Finally, the tooth coating applicator 10 is then removed from the interproximal space I.

Importantly, the tooth coating applicator 10 may be made only of the eleventh substrate 30 for applying the sealing agent to the dental surface S and for applying pressure on the sealing agent during its polymerisation. The other steps could then be performed without necessarily using the strip 11. Furthermore, some of these other steps may be omitted.

A teeth spacer may be used to facilitate the introduction of the strip 11 in the interproximal space S.

A dispensing apparatus (not shown) may be used to facilitate the insertion of the tooth coating applicator into the interproximal space I. The dispensing apparatus may comprise one or two reels around which the tooth coating applicator 10 may be disposed. The dispensing apparatus may take the form of a fork, similar to those used with dental floss, provided with two reels. The dispensing apparatus may be manually activated by the user such as by rotating a reel thereof with his/her thumb, while maintaining the tooth coating applicator 10 in contact on the dental surface S such as to successively bring each substrate contactingly along the dental surface S. If necessary, the user may then use his other hand to apply appropriate agents on the various substrates of the tooth coating applicator 10. This allows the user to more easily apply these agents, products or substances onto the substrates during the overall process as the user has one free hand. Alternatively, the reel(s) of the dispensing apparatus may be motorised.

The dispensing apparatus may also comprise some extensions to enable for the retention of isolating material, such as cotton rolls, to prevent the contamination of the interproximal dental area.

Another dispensing apparatus in a form of a small cylinder (not shown) may be used to store the invention for protecting it from contamination and to facilitate its dispensing. This apparatus is used with or without the previous apparatus.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

I claim:

1. A method for applying a sealing agent to an interproximal surface of a tooth, said method comprising:
   a) providing an elongated strip comprising a substrate which is configured to substantially conform to a shape of the interproximal surface to be treated;
   b) pre-forming said substrate substantially along the shape of the interproximal surface to be treated;
   c) applying said sealing agent to the substrate after the substrate has been pre-formed in the previous step;
   d) placing said pre-formed substrate and said sealing agent in contact with the interproximal surface; and
   e) handling said substrate such that at least a part of said sealing agent is transferred onto the interproximal surface.

2. A method as defined in claim 1, wherein in step e), said strip is slid along the interpromximal surface such that said sealing agent is applied onto the interproximal surface.

3. A method as defined in claim 1, wherein during step e), the method comprises applying pressure on said sealing agent during hardening thereof on the interproximal surface.

* * * * *